(12) United States Patent
Kalatz et al.

(10) Patent No.: US 6,925,393 B1
(45) Date of Patent: Aug. 2, 2005

(54) SYSTEM FOR THE EXTRAPOLATION OF GLUCOSE CONCENTRATION

(75) Inventors: Brit Kalatz, Ulm (DE); Udo Hoss, Sherman Oaks, CA (US)

(73) Assignee: Roche Diagnostics GmbH, Mannheim (DE)

( * ) Notice: Subject to any disclaimer, the term of this patent is extended or adjusted under 35 U.S.C. 154(b) by 116 days.

(21) Appl. No.: 09/711,855

(22) Filed: Nov. 13, 2000

(30) Foreign Application Priority Data

Nov. 18, 1999 (DE) .......................................... 199 55 734

(51) Int. Cl.$^7$ .......................... G06F 19/00; G01N 33/48; G01N 31/00
(52) U.S. Cl. .............................. 702/27; 702/19; 702/22
(58) Field of Search .............................. 702/27, 19, 22; 422/68.1; 703/11, 12

(56) References Cited

U.S. PATENT DOCUMENTS

| | | | |
|---|---|---|---|
| 4,731,726 A | 3/1988 | Allen, III | 364/416 |
| 5,019,974 A | 5/1991 | Beckers | 364/413.02 |
| 5,216,597 A | 6/1993 | Beckers | 364/413.02 |
| 5,507,288 A | 4/1996 | Bocker et al. | 128/633 |
| 5,542,420 A * | 8/1996 | Goldman et al. | 600/301 |
| 5,822,715 A | 10/1998 | Worthington et al. | 702/19 |
| 5,840,020 A | 11/1998 | Heinonen et al. | 600/309 |
| 5,997,475 A | 12/1999 | Bortz | 600/300 |
| 6,180,416 B1 | 1/2001 | Kurnik et al. | 436/518 |

FOREIGN PATENT DOCUMENTS

| | | |
|---|---|---|
| DE | 44 15 896 | 11/1995 |
| DE | 197 25 676 A1 | 12/1998 |
| EP | 0 834 825 | 4/1998 |
| WO | WO 97/28737 | 8/1997 |
| WO | WO 00/32258 | 6/2000 ............ A61M/5/00 |
| WO | WO-00/47109 A1 * | 8/2000 |

OTHER PUBLICATIONS

McGilvery et al. Biochemistry: A Functional Approach. W.B. Saunders Company, 1983, third edition, pp. 520–522 and 738–742.*
Walsh, J. et al. "STOP the Rollercoaster How to Take Charge of Your Blood Sugars in Diabetes", Torrey Pines Press, 1996 (pp. 123–125).
E.D. Lehmann et al. "An Integrated Approach for the Computer–Assisted Treatment of Diabetic Patients on Insulin", Med. Inform. (1992), vol. 17, No. 2, 105–123.
G. Freckmann et al. "Recent advances in continuous glucose monitoring", Exp Clin Endocrinol Diabetes 190 (2001) Suppl 2: S347–S357.

* cited by examiner

*Primary Examiner*—Ardin H. Marschel
*Assistant Examiner*—Cheyne Ly
(74) *Attorney, Agent, or Firm*—Jill L. Woodburn; Richard T. Knauer; Sujatha Subramaniam (57) ABSTRACT

A system for the extrapolation of a glucose concentration has a data input device for entering administered insulin doses and their times of administration, a data input device for entering the carbohydrates consumed or to be consumed, a unit for determining an actual glucose concentration at a point in time ($t_a$) in a patient's bodily fluid, a memory unit, and an evaluation unit for evaluation of the data stored in the memory unit, and for the extrapolation of a glucose concentration at a point in time $t_p$, whereby $t_p$ is after $t_a$ The extrapolation includes determining the portion ($I_{wirk}$) of insulin doses that become effective between $t_a$ and $t_p$; determining the portion of consumed carbohydrate units $KH_{wirk}$ that become effective between $t_a$ and $t_p$; and determining an extrapolated glucose concentration $G_p$ at the point in time $t_p$ with consideration for $I_{wirk}$ and $KH_{wirk}$.

8 Claims, 4 Drawing Sheets

Fig. 5

SYSTEM FOR THE EXTRAPOLATION OF GLUCOSE CONCENTRATION

CROSS-REFERENCE TO RELATED APPLICATIONS

This application claims priority under 35 U.S.C. §119 of German Application Serial No. DE 199 55 734.9 filed Nov. 18, 1999.

BACKGROUND AND SUMMARY OF THE INVENTION

This invention provides a system for the extrapolation of an actual glucose concentration in order to determine future glucose concentrations. Another configuration of the system uses extrapolated glucose concentrations to determine the proper dose of insulin to administer to a patient.

Diabetes mellitus is a group of chronic metabolic disorders characterized by raised blood glucose levels and impaired carbohydrate, fat, and protein metabolism. The insulin deficiency responsible for this disorder results from a defect in insulin secretion or the effect of insulin on the organism. Absolute insulin deficiency—which occurs in type I diabetes—is usually caused by an auto-immunological destruction of insulin-producing beta cells in the pancreas. These patients must rely on exogenous sources of insulin. Individuals with type II diabetes are resistant to insulin and suffer from impaired insulin secretion. Both of these disorders can occur to varying degrees. The exact causes of this disease are not known. Treatment of relative insulin deficiency ranges from dietary modifications and oral anti-diabetics to exogenous insulin administration.

Patients who suffer from Diabetes mellitus over the long term and, therefore, have chronic hyperglycemia, develop organ damage, impairment, and even failure. The eyes, kidneys, nerves, blood vessels, and the heart are affected in particular. Prevention of these late complications is the main goal of diabetes therapy. In the most commonly used therapy today, patients are administered slow-acting insulin that covers the basal insulin demand. They are also administered a bolus of normal insulin or a fast-acting insulin to offset the carbohydrates consumed during a meal.

This invention concerns the extrapolation of measured glucose concentrations to determine future concentrations in order to provide the patient with the basis for determining proper insulin dosage, or to properly control an insulin infusion pump.

A biostator is known in the prior art that is used to perform glucose measurements in venous blood and administer computer-controlled intravenous insulin and glucose infusions based on these measurements. A serious disadvantage of the biostator, however, is that intravenous infusions must be carried out to achieve proper regulation, and these infusions basically must be performed under stationary conditions. The patient cannot perform the infusion himself due to the high risk of infection.

The goal of development work, therefore, must be to maintain patients within a normal range of glucose concentration by means of subcutaneous insulin infusions that can be carried out by the patient himself or by means of implanted pumps. Due to the delayed effect of subcutaneously administered insulin, however, is it much more difficult to find a control procedure with which the goal can be achieved. U.S. Pat. No. 5,822,715 describes a diabetes management system with which an insulin dose to be injected by the patient is determined based on measured blood glucose values and previously administered insulin doses. To calculate the insulin dose to be administered, a future blood glucose value is calculated for this patient, and its deviation from a target blood glucose value is determined. This procedure only takes into consideration the administered insulin doses and their effectiveness profile, however. Other influences on blood glucose concentration are not explicitly taken into consideration. Our studies show that consideration of administered insulin quantities alone is not sufficient to keep glucose concentration within a normal range. It was found in particular that cases of strong hyperglycemia occur in regulating procedures based solely on this technique.

The object of the present invention was to propose a system for the reliable extrapolation of a glucose concentration and the determination of insulin doses to be administered subcutaneously. It was found with the invention that it is particularly important to take consumed carbohydrates into account when developing a regulating system that achieves the goal of subcutaneous insulin infusion. Accordingly, this invention provides a system for the extrapolation of glucose concentrations, comprising a data input device (EI) for entering the insulin doses ($I_i$) administered to the patient and their times of administration ($t_i$), data input device (EK) for entering the carbohydrates ($KH_j$) consumed or to be consumed by the patient, and the time they are consumed ($t_j$), a unit (GM) for determining the actual glucose concentration ($G_a$) in a patient's bodily fluid at a specific point in time ($t_a$), a memory unit (M) for storing the insulin doses administered and their times of administration, and the carbohydrates consumed and the times they were consumed, an evaluation device for evaluating the data stored in the memory unit and for extrapolating a glucose concentration at a point in time ($t_p$) that is later than the time of measurement ($t_a$), and whereby the extrapolation comprises the following steps:

determination of the portion ($I_{wirk}$) of insulin doses that take effect within the interval between measurement and the projected moment, determination of the portion ($KH_{wirk}$) of carbohydrates consumed that take effect within the interval between measurement and the projected moment, determination of an extrapolated glucose concentration ($G_p$) with consideration for the effective insulin doses ($I_{wirk}$) and the effective carbohydrate intake ($KHI_{wirk}$).

A system according to the invention comprises a data input device (EI) for entering administered insulin doses and their times of administration. This data input device can be a keyboard, for instance, by means of which the patient himself enters the insulin dose that he administered or had administered. The time of administration can be entered manually as well. The data input device could also be combined with a clock so the patient has the option of selecting time of input as the time of administration. It is also possible to combine a device that performs the administration, e.g., an automatic insulin pump, with a transmission device that transmits the administered insulin dose and its time of administration to the data input device. This transmission can take place over a fixed wire or via telemetric connection. It is also possible that the patient operates an infusion device himself, such as an insulin pump outfitted with a transmission unit that transmits the administered insulin dose along with the time of administration to the data input device.

The system also comprises a unit (GM) that determines a glucose concentration at a specific point in time. Blood glucose meters are known in the prior art with which glucose concentration can be measured in a capillary blood sample collected by the patient from the fingertip and then applied to a test element, for instance. These devices will not be described in further detail because they have been known for some time. To determine blood glucose values, it is also possible to implant measurement sensors in the body (e.g., intravasal, interstitial). This technology has not become popular because the sensors tend to drift. Another possibility for the determination of glucose values is based on measurements in interstitial fluid. Devices are known, for instance, with which small quantities of interstitial fluid can be collected through thin cannula and then analyzed. To perform subcutaneous measurements it is also possible to implant miniaturized catheters with which microdialysis or ultrafiltration can be performed, so that measured results can be provided at close intervals. A device based on microdialysis is described in U.S. Pat. No. 5,174,291, for instance. A device based on the principle of ultrafiltration is described in U.S. Pat. No. 4,777,953. These devices will not be discussed in further detail here.

The carbohydrates consumed by the patient and their time of consumption are recorded by a second data input device (EK). However, data input devices for insulin doses and carbohydrates can be provided by the same physical device, e.g. a keyboard, for entering both, administered insulin doses as well as consumed carbohydrates. Currently, diabetics typically estimate their insulin demand themselves based on the quantity of carbohydrates they consumed or are planning to consume, and then inject themselves with the calculated insulin dose before or directly after eating. The diabetic determines carbohydrate units by calculating the number of bread exchanges using tables for different types of food. According to the invention, the diabetic, nurse, or another caregiver enters the number of carbohydrate units or bread exchanges determined in the second data input device. This can be accomplished using a keyboard that is part of the system, for instance. Since the determination of carbohydrates consumed or to be consumed is relatively inaccurate by nature, one can use preprogrammed keys to enter a small, normal, or heavy meal, instead of a numerical entry. The system assigns 2, 4, or 6 carbohydrate units to these keys, for instance, which are used in the formula described below. It is also possible to provide selection keys or a selection field with which values in bread exchange increments of 0.5 can be entered. It is important that the times of carbohydrate consumption also be entered as accurately as possible. To ensure this, a clock can be provided in the data input device or the system that selects the time of input as the time of carbohydrate consumption and pairs it with the value of carbohydrate units consumed. The system should also provide an option for the user to change this time or to enter it himself directly if necessary.

The system also comprises a memory unit (M) for storage of administered insulin doses and their times of administration, as well as carbohydrate units consumed and their times of consumption, so they can be used as the basis for a subsequent evaluation. Such memory components—known as RAM—have been known for some time in the prior art.

An important component of the present system is an evaluation unit for the evaluation of data stored in the memory unit according to a predetermined evaluation procedure. As mentioned previously, the evaluation unit performs an extrapolation, by means of which a future glucose concentration ($G_p$) is determined. It was found that such an extrapolated glucose concentration is a suitable control variable for the determination of required insulin or glucose doses, and for the early detection of hypoglycemia or hyperglycemia. The extrapolation includes the determination of the portion of insulin dose that will become effective in the interval between measurement and the extrapolated point in time, and the determination of the portion of the carbohydrates consumed that takes effect in this time interval. In accordance with the invention it was found that these two parameters are the most important, and that taking them into account leads to an extrapolated glucose concentration that allows for a sufficiently exact determination of future glucose concentrations and required insulin doses. The effectiveness of the determination procedure based on this method will be demonstrated later using experimental data.

The portion ($I_{wirk}$) of insulin doses that become effective in the interval between the actual measurement ($t_a$) and the extrapolated point in time ($t_p$) can be determined by taking into account the kinetics of effectiveness of the insulin used.

DETAILED DESCRIPTION OF THE DRAWINGS

Figure 1:
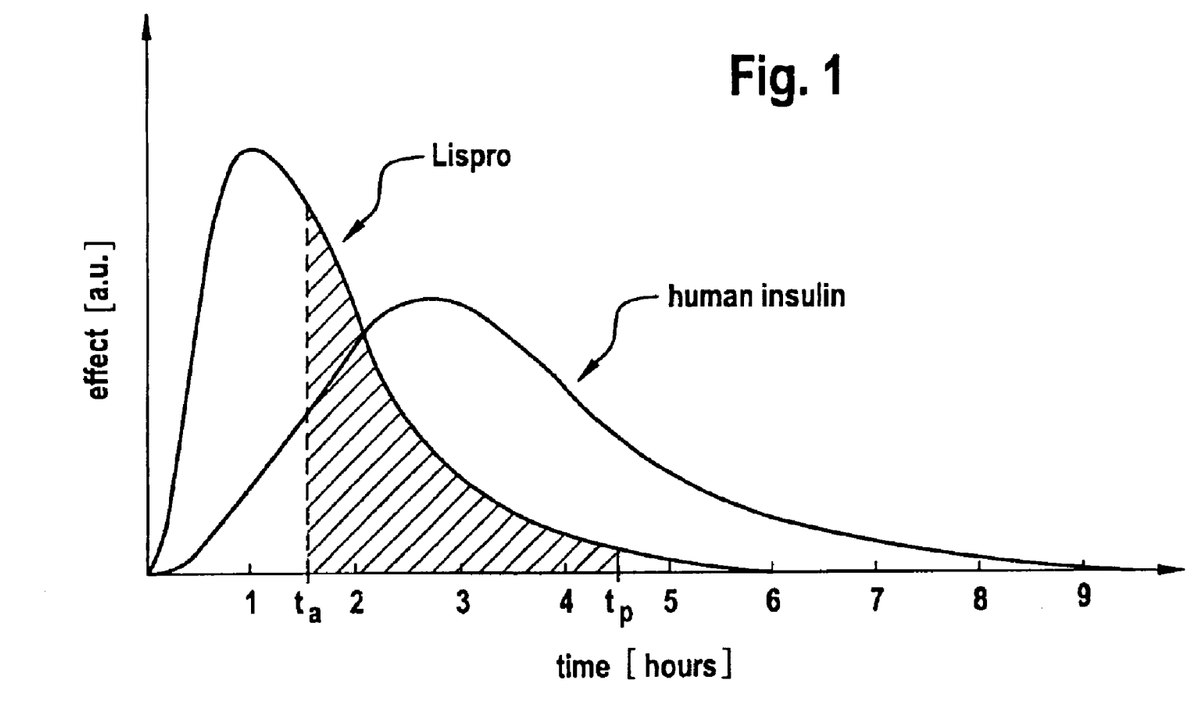
FIG. 1 is a profile showing the effectiveness of human insulin and Lispro.

FIG. 1 shows effectiveness profiles of human insulin and Lispro after subcutaneous injection. Systems based on the present invention are especially well-suited for use with fast-acting insulins such as Lispro and Aspart.

The portion of insulin that takes effect in the period between measurement and the projected point in time can be calculated by first determining how much time has passed since administration of the insulin and the current point in time. In FIG. 1, for instance, the measurement ($t_a$) occurred 1.5 hours after insulin infusion. Three hours was selected as the projection period, so $t_p$ can be found at 4.5 hours on the time axis shown. The portion of the insulin that is effective in the projection period can be determined by integrating the curve between $t_a$ and $t_p$ and multiplying this value by the number of insulin units administered. This method of calculation is based on the fact that the insulin effectiveness curve is scaled in such a way that the area under the complete curve is 1 (one), so that the integral between two points in time provides the portion directly that takes effect in the period involved. If numerous insulin doses make a contribution within the projection period, this is taken into account by adding up the individual contributions by using the calculation procedure described for each insulin dose individually. It is also possible to take contributions from different types of insulin into account by basing the calculation on the effectiveness profile of each type. A calculation formula that takes into account numerous insulin doses—of the same type of insulin, however—is as follows:

$$I_{wirk} = \sum_{i=1}^{n} \int_{t_a}^{t_o} C_1(t)\,dt * I_i \qquad (1)$$

In the formula above, C stands for the portion of insulin that is bioavailable at the time t, which corresponds to the value of the ordinate in FIG. 1. The factor $I_i$ indicates the dose administered via injection i. The zero point in time for each addend is the time of administration of the respective insulin dose. n indicates the number of insulin doses taken into account in the calculation. Which insulin doses are taken into account depends on the effectiveness profile of the insulin used and the time interval between administration and the actual point in time $t_a$. FIG. 1 indicates that the effect of Lispro has worn off 6 hours after administration. This means that doses of Lispro that are administered more than 6 hours before the current point in time do not need to be taken into account.

In practice, the integration indicated in formula (1) can be greatly simplified if the insulin effectiveness profile is approximated by a linear increase and a linear decrease. The experimental results shown below are based on such an approximation and show that this is a feasible method for practical use. For purposes of the present invention, the integral representation used in formula (1) stands for all types of determination that—either directly or indirectly—determine a portion of the insulin that will become effective in the projection period by integrating an effectiveness profile. As an example, it is also possible to use a function (transformation) $F_I(t)$ for this purpose:

$$F_1(T) = \int_0^T C_1(t)\,dt \qquad (2)$$

$F_I(T)$ indicates the portion of insulin that takes effect from the moment of injection until the point in time T. The portion of insulin that takes effect in the projection period is determined with the transformation as follows:

$$I_{wirk} = F_I(t_p) - F_I(t_a) \qquad (3)$$

By storing the integral function $F_I$ (e.g., in a table), the subsequent calculation of $I_{wirk}$ can be traced back to a simple substraction.

Figure 2:
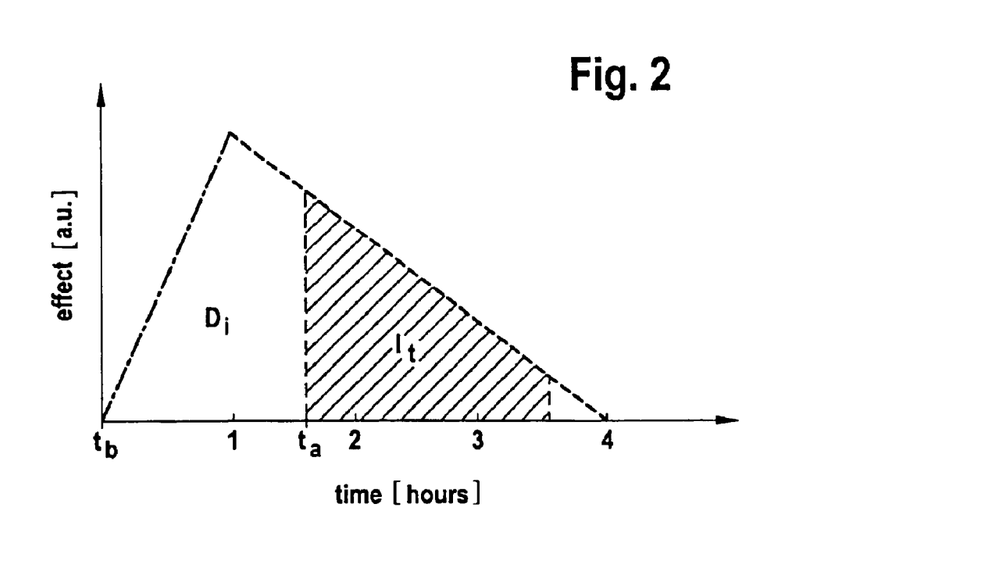
FIG. 2 is a profile showing an approximation of the effectiveness of a fast-acting insulin using a triangulation function.

FIG. 2 shows an approximation of the effectiveness profile using a triangulation function. Insulin was administered at the point in time $t_b$, and the glucose concentration was measured at the point in time $t_a$. A projection period of 2 hours was selected. The shaded triangular area therefore corresponds to the portion of insulin that is effective in the projection period.

As described earlier, the system was improved considerably by taking into account the quantity of carbohydrates that is effective in the projection period. If a carbohydrate effectiveness profile ($C_{KH}(t)$) that is known or assumed to be valid is used as the basis, the effective portion of carbohydrates is determined as follows:

$$KH_{wirk} = \sum_{j=1}^{m} \int_{t_a}^{t_p} C_{KH}(t)\,dt * KH_j \qquad (4)$$

This formula uses the factor $KH_j$ to take into account the consumption of carbohydrates at numerous points in time, as well as the quantity of carbohydrate units consumed each time. The zero point in time is represented in this case by the time of carbohydrate consumption. The integration indicated in formula (4) stands for all types of determination that—either directly or indirectly—determine a portion of the carbohydrates that will become effective in the projection period by integrating a carbohydrate effectiveness profile, as in formula (1). Due to the commonly used scaling, $$\int_0^\infty C_{KH}(t)\,dt = 1$$

this also includes methods in which integration of the curve outside the projection period and subtraction of this integral is used determine the effective portion of insulin in the projection period. The complex integration can be eliminated when calculating the carbohydrates that are effective within the projection period if an idealized carbohydrate effectiveness profile is used as the basis, or if the same approach is used to determine the effective portion of insulin using a transformation $F_{KH}(T)$:

$$F_{KH}(T) = \int_0^T C_{KH}(t)\,dt \qquad (5)$$

$KH_{wirk}$ is calculated as follows:

$$KH_{wirk} = F_{KH}(t_p) - F_{KH}(t_a), \qquad (6)$$

whereby $t_p$ and $t_a$ are determined based on carbohydrate consumption. The effectiveness of the carbohydrates in the organism is given by the glucose "flooding". Glucose "flooding" describes the appearance of glucose in the organism that can be measured, e.g., in blood, after food intake or as a result of hepatic glucose production. Glucose flooding itself depends on various factors. It is known to be affected by the stomach emptying rate, the glucose absorption rate from the duodenum, and the degree of hepatic glucose consumption. It was found, however, that the stomach emptying rate is the step that controls the speed of glucose "flooding". It was also found in carbohydrate absorption studies that glucose flooding increases quickly at first, plateaus briefly (10), then drops slowly (12). A time of between 10 and 25 minutes and, most preferably, about 15 minutes, is selected as the delay between carbohydrate consumption and the onset of glucose flooding. The plateau (10) of glucose flooding is preferably selected as 15 to 25% of the total period of glucose flooding ($t_{KH}$), which is indicated as follows:

$$t_{KH} = Q * KH_j \qquad (7)$$

whereby Q is a factor in the range of 2 to 10 min/g and preferably 5 min/g, and $KH_j$ is the quantity of carbohydrates consumed in grams.

Figure 3:
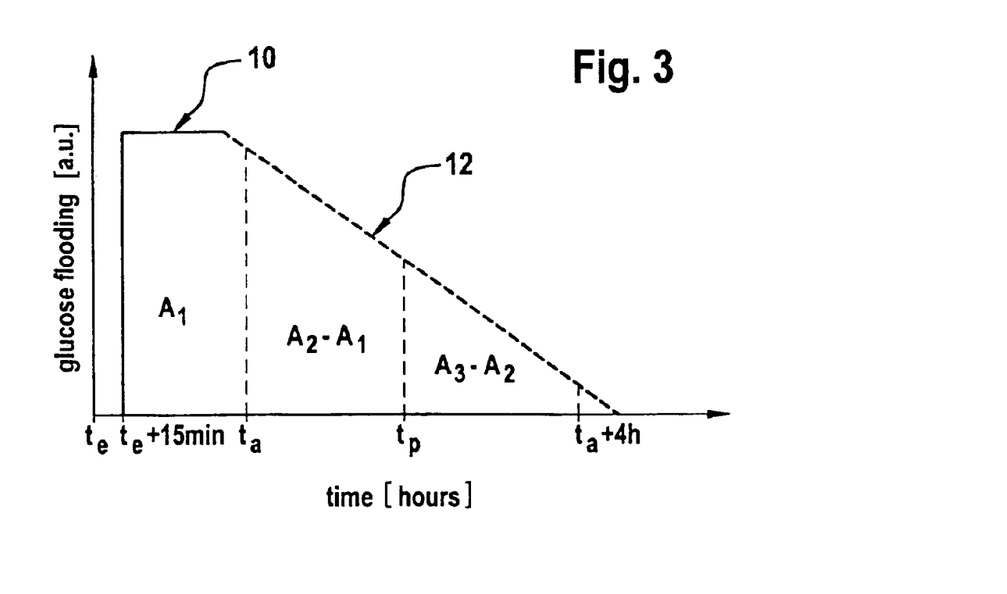
FIG. 3 is a model of glucose flooding rate after a meal.

FIG. 3 shows a model that was used as a basis in subsequent experiments. In FIG. 3, the moment of carbohydrate consumption is indicated as $t_e$, and the time of measurement is indicated as $t_a$. The time to which the glucose concentration should be projected is indicated as $t_p$. The portion of effective carbohydrates is therefore shown as the area described as $A_2 - A_1$.

The present invention can be used with different models of the glucose flooding rate. Based on the experiments conducted, however, it was found that the course of glucose flooding shown in FIG. 3 forms a good basis for the extrapolation of glucose concentration. The shape of the curve shown in FIG. 3 is determined by the following parameters:

Time interval ($t_z$) between carbohydrate consumption and the onset of glucose flooding, the duration of the plateau ($t_{PLATEAU}$), and the duration ($t_{DROP}$) of the drop in glucose flooding. The following parameters empirically were found to be especially favorable:

$$t_z = 15 \text{ min}$$

$$t_{PLATEAU} = 0.2 * t_{KH}$$

$$t_{DROP} = 0.8 * t_{KH}$$

The entire area below the glucose flooding curve was scaled as 1. The slope of the drop is therefore determined by the height of the plateau and the duration of the drop. The effective carbohydrates ($KH_{wirk}$) can therefore be determined based on an entire area of 1.

The extrapolated glucose concentration can be calculated as follows based on the insulin doses that are effective in the projection period ($I_{wirk}$) and the carbohydrate units ($KH_{wirk}$) that are effective in the projection period:

$$G_p = G_a - I_{wirk} \cdot D * SE + KH_{wirk} * E + X \qquad (8)$$

As a prerequisite for this formula it is assumed that the actual glucose concentration ($G_a$) at the time of measurement is decreased proportionally to the patient's insulin sensitivity by the effective insulin units in the projection period. This proportionality is taken into account by the empirical weighting factor D which, according to experiments, is between 0.05 and 0.5 mmol/l/g. Insulin sensitivity means simply the quantity of carbohydrate units that can be compensated by one unit of insulin. Insulin sensitivity fluctuates depending on the time of day, and is dependent on other physiological factors as well. In practice, however, simply estimating a patient's insulin sensitivity has become very significant, because the patient can use it to calculate the approximate quantity of insulin that he must inject to offset the glucose flooding expected after an upcoming meal. To do this, the patient uses tables to determine the number of bread exchanges (equivalent to carbohydrate units) that he will consume at the meal and multiplies this value by his estimated insulin sensitivity in order to calculate his insulin dose.

Formula 8 is also based on the fact that the actual glucose value ($G_a$) in the projection period is increased proportionally to the carbohydrate units that are effective in this period. This proportionality is taken into account with the factor E. It was found that it is favorable to use $R_{KH} * F$ as E, whereby F is a factor close to 0.25 mmol/l/g, and $R_{KH}$ is the carbohydrate reduction factor. The carbohydrate reduction factor is used to reduce the effect of carbohydrates on blood glucose concentration in the calculation.

The additive variable X in formula 8 can be determined based on empirical studies. However, $G_{basal} = I_{basal} * SE * C$ is preferably used as X. In this case, X takes into account the fact that blood glucose is also increased by basal insulin demand ($I_{basal}$) during the projection period. This increase in glucose concentration is considered to be proportional to insulin sensitivity, whereby the empirical weighting factor C takes this proportionality into account. C is preferably between 0.05 to 0.5 mmol/l/g.

In addition or as an alternative, the variable X can contain the variable $SG*A$ as the addend. SG (unit: mmol/l/g) corresponds to the increase in glucose concentration at the time of measurement ($t_a$), and A is an empirical weighting factor that is preferably between 0 and 100 min.

As described earlier, a main goal of this invention is to keep a patient's glucose concentration within a normal range. Although most experts consider the normal range to be a glucose concentration of between 3.5 and 10 mmol/l, others disagree. These values should therefore be considered to be guide values. A system based on the present invention can contain a warning unit that compares the extrapolated glucose concentration ($G_p$) with a programmed normal range and sounds a warning signal when the extrapolated glucose concentration lies outside this range.

A system based on this invention can also include a control unit that controls an insulin infusion device such as an insulin pump. The system can also have a display or another type of output device that is used to suggest an insulin dose to the patient which he then administers himself or has administered. It is especially favorable if the insulin is infused automatically by the device but the patient can control it if necessary. This can be achieved by including a release unit in the system that the patient can use to intentionally release an insulin dose suggested by the system. For instance, the system can display a calculated insulin dose and wait for a key to be pressed before it administers the insulin (e.g., using an insulin pump).

The insulin dose (ID) can be calculated based on the following formula:

$$ID = ((G_P - G_R)/SE * E) + Y \qquad (9)$$

In formula 9, $G_p$ stands for the extrapolated glucose concentration, and $G_R$ represents a target glucose concentration within the normal range or a maximum acceptable glucose concentration. The formula also contains the patient's insulin sensitivity (SE), the empirical factor E, and an additive variable Y. Experiments have shown that $R_{KH} * KH_{Rest}/SE*F$ is a favorable choice for Y. In this formula, $R_{KH}$ represents the carbohydrate reduction factor. $KH_{Rest}$ is the quantity of carbohydrates resorbed between the actual time ($t_a$) and the end of effectiveness of the insulin dose that was administered. The effective period ($T_i$) for Lispro is about 4 hours, and about 6 hours for human insulin from the time of administration. In terms of the present invention, values are included for the effective period ($T_I$) of insulin for which the integral $$\int_0^{T_1} C_1(t) dt \text{ is between 0.8 and 1.}$$

This approach also takes into account carbohydrate effects that take place after the projection period.

It has proven to be advantageous to design a system based on the present invention with an automatic measuring device for determining glucose concentration with which measurements can be performed at regular intervals without user intervention. The current glucose concentration and insulin dose to administer are preferably determined at intervals of between 1 and 30 minutes. As mentioned earlier, this type of quasi continual monitoring of glucose concentration can be performed especially well with a microdialysis system. An insulin infusion device can be integrated in such a system or in other sensors. The advantage of this design is that just one unit need be implanted in the patient's body.

The design and function of a system based on the invention for extrapolation of a glucose concentration or for determination of an insulin dose to be administered is described in greater detail using the following figures:

FIG. 1: Effectiveness profile of human insulin and Lispro

FIG. 2: Approximation of the effectiveness profile of a fast-acting insulin using a triangulation function FIG. 3: Model of glucose flooding rate after a meal FIG. 4: Schematic representation of the system units FIG. 5: Glucose/time profile and administered insulin doses, and quantities of carbohydrates consumed FIGS. 1 through 3 were described in the text above.

Figure 4:
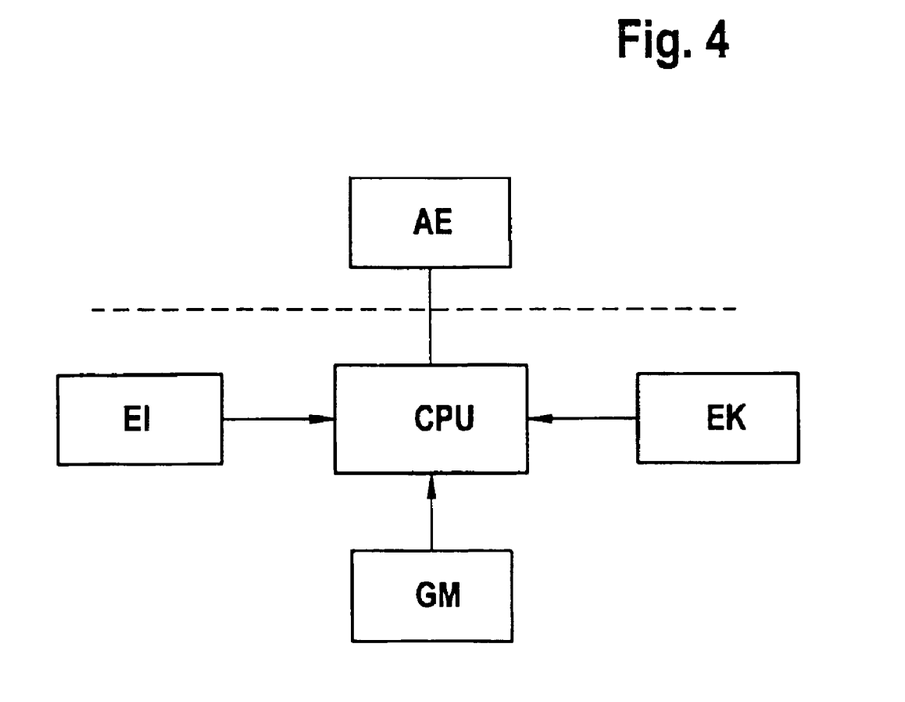
FIG. 4 is a schematic representation of the system units.

FIG. 4 shows the schematic representation of a system based on the present invention. A first data input device (EI) communicates the insulin doses, types, and times of administration to the evaluation unit (CPU). As described above, the data input device can be a keyboard or another type of device for manual data input. It can also be a data input device that receives signals from another device such as an insulin pump. The evaluation unit also receives data on the carbohydrates consumed and their times of consumption from a second data input device (EK). The second data input device can also be a keyboard (e.g. the same as for the first data input device) or another type of device for manual input of data. An option can also be included for specifying the type of food consumed in such a way that describes how its carbohydrate reduction factor or its resorption by the organism takes place over time. It was found, for instance, that dextrose is resorbed and initiates glucose flooding much more quickly than highly fatty meals, for instance.

FIG. 4 also shows that the evaluation unit receives data from the unit (GM) to determine an actual glucose concentration. These data do not necessarily have to be individual glucose concentrations. It can also be designed to transmit all the values measured at different intervals over a specified period of time collectively. The transmitted glucose concentration values can be calculated in the evaluation unit in order to determine the slope of the glucose concentration. This calculation can also be carried out in the GM unit, however, and these data can be transferred to the evaluation unit.

As illustrated in the previous description, the evaluation unit (CPU) uses the information received to determine a future glucose concentration and/or an insulin dose to be administered. The units shown below the dotted line in FIG. 4 constitute a system according to the invention. The output unit (AE) shown above the dotted line is optional, however. The output unit can be a display, for instance, that displays the extrapolated glucose concentration or an insulin dose to be administered. As an alternative, future glucose concentrations can also be determined for a number of different points in time, and the resulting curve can be displayed. An output unit can also be a warning unit that warns the patient about an impending hypoglycemic or hyperglycemic condition if the extrapolated glucose value is outside the prescribed normal range. An insulin infusion device such as an insulin pump can also be used as the output unit, so that the evaluation unit initiates the administration of insulin either directly or by means of a control unit with the administration device. As described above, the system can also be designed so that the user or caregiver has the option of approving administration of the insulin dose.

Figure 5:
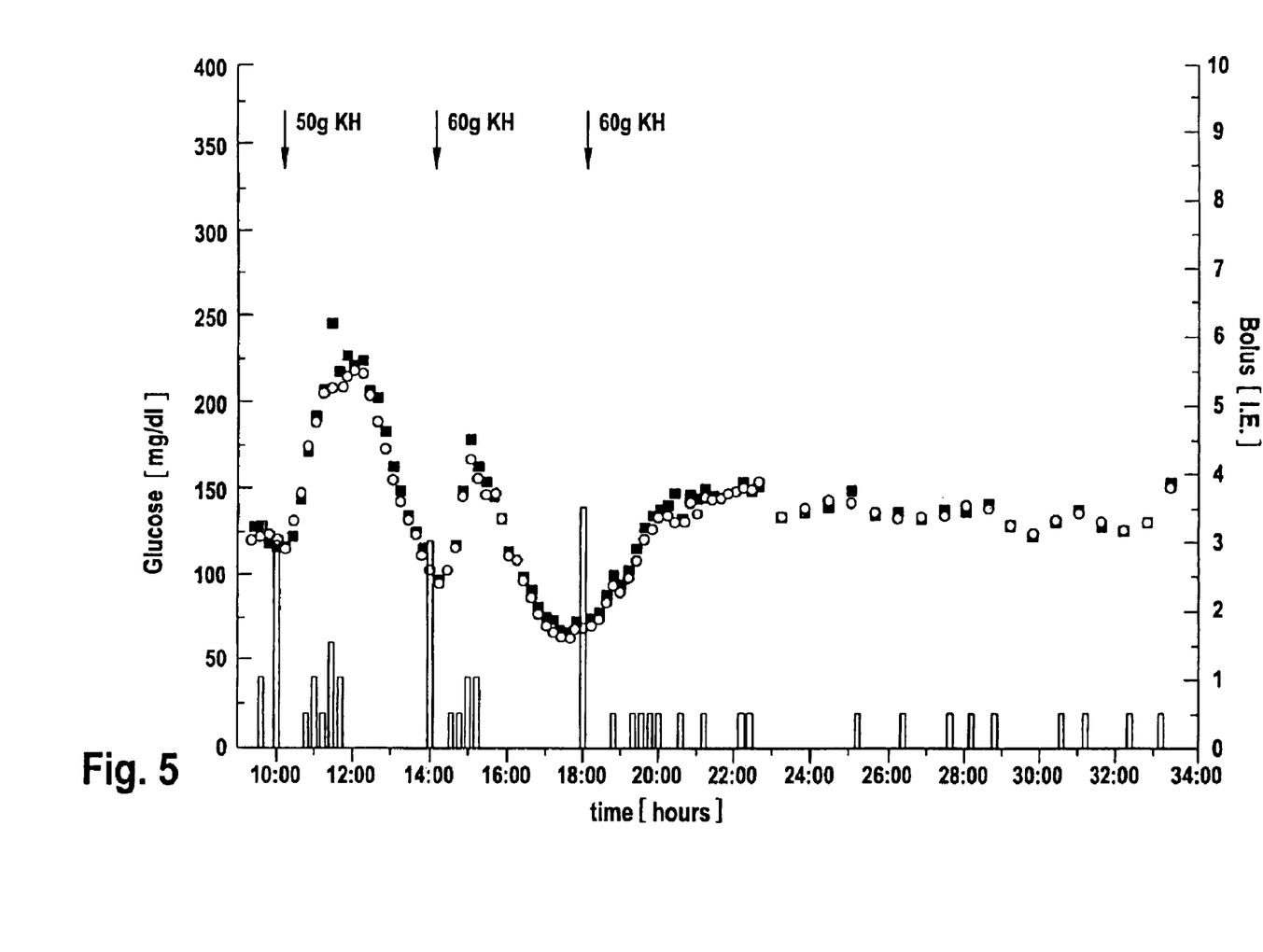
FIG. 5 is a glucose/time profile and administered insulin doses, and quantities of carbohydrates consumed.

FIG. 5 shows a 24-hour study in which blood samples were drawn from a patient at 12 and 36-minute intervals. The glucose concentration of these samples was then tested on a Glucotrend from Roche Diagnostics GmbH and an Hitachi 911 automated analyzer. The black squares in FIG. 5 represent the blood glucose concentrations measured with the Glucotrend (shown on the left ordinate), and open circles represent the concentrations measured on the Hitachi analyzer. FIG. 5 also shows 3 meals consisting of 50, 60, and 60 [sic] grams of carbohydrates at the times indicated by the arrows. Insulin doses were calculated and administered based on calculations using formula 9 while taking into account an insulin effectiveness kinetic according to FIG. 2 and a glucose flooding rate according to FIG. 3. These insulin doses and administrations are represented by empty bars in FIG. 5. The insulin dose administered in each case is indicated by the height of the bars on the right ordinates.

FIG. 5 shows that blood glucose concentration increases significantly after meals and cannot be completely compensated by previous insulin doses. It also shows that the insulin doses helped to limit the increase in blood glucose concentration to values below 225 mg/dl. After the third meal, the insulin doses helped achieve a stable blood glucose concentration of about 150 mg/dl. FIG. 5 also indicates the glucose concentrations are relatively low before the meals, but the regulation algorithm was capable of limiting the insulin doses in such a way that no instances of significant hypoglycemia occurred. Accordingly, systems based on the present invention for extrapolating a glucose concentration and for determining insulin doses to be administered represent a promising opportunity to provide the diabetic with help in his therapy, and to develop systems that administer insulin automatically.

What is claimed is:

1. System for the determination of a glucose concentration, comprising:
    a data input device for entering insulin doses administered ($I_i$) and their times of administration ($t_i$),
    the same or a second data input device for entering carbohydrates ($KH_j$) consumed or to be consumed, and their times of consumption ($t_j$),
    a unit for measuring the actual glucose concentration ($G_a$) in a patient's bodily fluid at a specific point in time ($t_a$),
    a memory unit for storing administered insulin doses and their times of administration, and carbohydrates consumed and their times of consumption,
    an evaluation device for evaluating the data stored in the memory unit and extrapolating a glucose concentration at a point in time ($t_p$), whereby $t_p$ is after $t_a$, and the extrapolation comprises the following steps:
    determination of the portion ($I_{wirk}$) of insulin doses that take effect within the interval between $t_a$ and $t_p$,
    determination of the portion ($KH_{wirk}$) of carbohydrates consumed that take effect in the interval between $t_a$ and $t_p$, and
    determination of a glucose concentration $G_p$ at the point in time $t_p$ using $I_{wirk}$ and $KH_{wirk}$, wherein
    the portion of insulin doses ($I_{wirk}$) that take effect in the period between $t_a$ and $t_p$ is calculated using the following formula $$I_{WIRK} = \sum_{i=1}^{n} \int_{t_a}^{t_p} C_1(t)\,dt(I_i);$$

$n$ = number of insulin doses to be considered whereby $C_I$ represents the quantity of insulin that is bioavailable at the point in time $t$ and therefore represents the insulin effectiveness profile; with $$\int_0^\infty C_1(t)\,dt = 1.$$

2. System according to claim 1, in which the unit used to measure the actual glucose concentration $G_a$ is a microdialysis device.

3. System according to claim 1 that also includes a display unit for displaying the glucose concentration $G_p$.

4. System according to claim 1 that also includes a warning unit that emits a warning signal when the glucose concentration $G_p$ is outside a selected normal range.

5. System according to claim 1 in which a user enters the carbohydrate units consumed ($KH_j$).

6. System according to claim 1 in which the system contains a control unit for an insulin infusion device or is connected to such a device, and in which the insulin doses administered ($I_i$) and their times of administration ($t_i$) are transmitted from the control unit to the date input device for entering insulin doses.

7. System according to claim 1, in which the point in time $t_p$ is from 0.5 to 5 hours after $t_a$.

8. System according to claim 1, in which the point in time $t_p$ is at least 2 hours after $t_a$ and up to 4 hours after $t_a$.

* * * * *